United States Patent
McConnell

(10) Patent No.: US 8,430,859 B2
(45) Date of Patent: Apr. 30, 2013

(54) PURGE BAG FOR AN IV LINE AND METHODS OF ADDRESSING THE CAUSES OF THE GROWTH IN RESISTANT BACTERIAL INFECTIONS IN HOSPITALS

(76) Inventor: Sandra M. McConnell, Hobe Sound, FL (US)

( * ) Notice: Subject to any disclaimer, the term of this patent is extended or adjusted under 35 U.S.C. 154(b) by 291 days.

(21) Appl. No.: 12/270,836

(22) Filed: Nov. 13, 2008

(65) Prior Publication Data

US 2009/0137978 A1    May 28, 2009

Related U.S. Application Data

(60) Provisional application No. 60/987,816, filed on Nov. 14, 2007.

(51) Int. Cl.
*A61J 1/10*     (2006.01)
*A61J 1/12*     (2006.01)
*A61M 39/00*    (2006.01)
*A61M 39/10*    (2006.01)
*A61M 39/20*    (2006.01)
*A61M 39/22*    (2006.01)

(52) U.S. Cl.
USPC ........... 604/408; 604/403; 604/407; 604/411; 604/415; 604/500

(58) Field of Classification Search ............ 604/82, 604/83, 122, 247, 251, 260, 262, 407, 408, 604/411, 415, 500, 403; 222/108, 130; 128/203.12, 128/205.24, 205.25
See application file for complete search history.

(56) References Cited

U.S. PATENT DOCUMENTS

| | | | | |
|---|---|---|---|---|
| 3,699,964 | A * | 10/1972 | Ericson | 604/33 |
| 4,248,223 | A * | 2/1981 | Turner et al. | 604/507 |
| 4,300,572 | A * | 11/1981 | Knighton | 600/487 |
| 4,393,880 | A * | 7/1983 | Taylor | 600/573 |
| 4,863,452 | A * | 9/1989 | Irmiter et al. | 604/408 |
| 5,061,236 | A * | 10/1991 | Sutherland et al. | 604/6.09 |
| 5,289,858 | A * | 3/1994 | Grabenkort | 141/97 |
| 5,538,638 | A * | 7/1996 | Hedman | 210/636 |
| 5,897,526 | A * | 4/1999 | Vaillancourt | 604/82 |
| 6,179,823 | B1 * | 1/2001 | Niedospial, Jr. | 604/408 |
| 6,287,289 | B1 * | 9/2001 | Niedospial, Jr. | 604/408 |
| 2002/0143294 | A1 * | 10/2002 | Duchon et al. | 604/131 |
| 2002/0177837 | A1 * | 11/2002 | Barnitz | 604/416 |
| 2005/0234407 | A1 * | 10/2005 | Spohn et al. | 604/253 |
| 2007/0156118 | A1 * | 7/2007 | Ramsey et al. | 604/533 |
| 2009/0076433 | A1 * | 3/2009 | Folden et al. | 604/4.01 |

* cited by examiner

*Primary Examiner* — Tatyana Zalukaeva
*Assistant Examiner* — Adam Marcetich
(74) *Attorney, Agent, or Firm* — William D. Hare; Vandana Awasthi; McNeely, Hare & War LLP

(57) ABSTRACT

The invention relates to systems and methods for collecting the content of IV lines that otherwise would be spilt in a hospital environment. In one general aspect the system includes an intravenous tubing system to prevent spillage of fluids. The IV tubing system includes intravenous tubing and a purge bag. The intravenous tubing includes a first end configured to attach to a fluid container and a second end having a connector. The purge bag includes at least one port, such as a needle-free valved port, configured to receive fluids from the intravenous tubing. The purge bag optionally contains a second port is configured to let air into or out of the purge bag with a closing means that may be a needle-free valved port. The purge bag can be packaged separately from the IV tubing set and the package can be opened at the time of use.

9 Claims, 6 Drawing Sheets

PURGE BAG FOR AN IV LINE AND METHODS OF ADDRESSING THE CAUSES OF THE GROWTH IN RESISTANT BACTERIAL INFECTIONS IN HOSPITALS

CROSS-REFERENCE TO RELATED APPLICATIONS

This application claims priority from U.S. Provisional Patent Application No. 60/987,816, filed on Nov. 14, 2007, the contents of which are incorporated herein by reference in their entirety.

TECHNICAL FIELD

The field of the invention generally relates to an intravenous purge bag and its use to catch fluids, such as blood, blood products, chemotherapy, pharmaceuticals such as antibiotics, etc., that are otherwise spilt in hospitals. By catching the contaminated fluids, the intravenous purge bag will reduce the growth and creation of resistant bacteria and hospital-acquired infections otherwise caused by the spillage of these contaminated fluids.

BACKGROUND

There is a need to decrease infections in U.S. hospitals as they are increasing in frequency and creating costs to hospitals, the government and consumes. One recent report in *Clinical Infectious Diseases* and reported in *Science Daily* stated that a review of inpatient data from U.S. hospitals shows that the number of infections caused by a common bacterium increased by over 7 percent each year from 1998 to 2003. The corresponding economic burden to hospitals increased by nearly 12 percent annually. One bacterium, *Staphylococcus aureus* (also known as staph) is a significant cause of a wide range of infectious diseases in humans, ranging from minor skin infections to life-threatening diseases such as pneumonia and meningitis. According to the report, in 1998, U.S. hospitals reported a little more than a quarter-million staph infections and slightly over 7 percent of those patients died. By the final year of the study, 2003, hospitals reported nearly 390,000 infections, representing 1 percent of that year's inpatient stays.

The report suggests that one possible reason for the increase in infections is the documented increase of an antibiotic-resistant staph infection known as methicillin-resistant *Staphylococcus aureus* (MRSA). Interestingly, the report notes that staph-related in-hospital mortality rate dropped by almost 5 percent each year, which may be the result of the introduction of more stringent infection control programs or due to appropriate early treatment of MRSA infections with an effective antibiotic. Nonetheless, hospital expenditures associated with staph infections are substantial, increasing from $8.7 billion in 1998 to $14.5 billion in 2003. This cost includes such factors as extended length of hospitalization and additional surgery, medications, lab tests, and radiologic studies.

SUMMARY

In one general aspect, the invention is an intravenous tubing system to prevent spillage of fluids. The tubing system includes intravenous tubing and a purge bag. The intravenous tubing includes a first end configured to attach to a fluid container and a second end having a connector. The purge bag has at least one port configured to attach to the connector and receive fluids from the intravenous tubing, the port being openable to attach to the connector and closable after removal of the connector.

Embodiments of the tubing system may include one or more of the following features. For example, the purge bag may further include a second port configured to be opened and closed to let air pass through the second port. The second port may include a closing means to prevent fluid flow through the second port. The closing means may be one or more of a valve, needle-free valve, cap, lid, clamp, and heat sealer.

The first port may include a closing means to close the port to prevent fluid flow through the first port out of the purge bag. The closing means may be one or more of a valve, needle-free valve, cap, lid, clamp, and heat sealer. The IV purge bag may be a bag having an inner volume and the port may be closed into the inner volume in a first state but open into the inner volume upon connecting a tubing to the port.

In another general aspect, the invention is an IV purge bag for receiving purged fluids from an IV tubing set. The IV purge bag includes a bag having an inner volume, a first port and a second port. The first port is in a closed configuration into the inner volume but in an opened or openable configuration into the inner volume upon connecting tubing to the first port and configured to connect to and receive fluids from an IV tubing set. The second port is in a closed configuration but opened or openable into the inner volume from outside the bag to allow the flow of air through the port. Embodiments of the IV purge bag may include one or more of the features described above or here. For example, the first port may include a valve and the second port may include a valve. The valves may be needle-free valves.

In another general aspect, the invention is a method of purging an IV tubing system. The method includes:

providing a purge bag, attaching intravenous tubing to a fluid container containing a fluid to be administered to a patient, and purging a portion of the contents of the fluid in the intravenous tubing through the port into the purge bag. The purge bag has at least one port configured to receive fluids from the intravenous tubing attachable to a fluid container at one end and attachable to the purge bag at another end. The port is openable to receive fluids from the intravenous tubing into the purge bag and closable to prevent flow of fluids out of the purge bag through the port.

Embodiments of the method may include one or more of the following features. For example, the IV tubing set and the purge bag may be provided with the connector of the IV tubing set connected to the at least one port of the purge bag. The IV tubing set and the purge bag may be provided unconnected and the connector of the IV tubing set may be connected to the at least one port of the purge bag.

The method may further include purging fluid and air in the IV tubing set into the purge bag until the IV tubing set is free of air in a line passing between the bag containing a fluid and the second end of the IV tubing set. The method may still further include disconnecting the purge bag from the IV tubing set, closing the port and discarding the purge bag without fluid escaping from the purge bag through the port.

The first port may include a closing means to close the port to prevent fluid flow through the first port out of the purge bag. The closing means may include one or more of a valve, needle-free valve, cap, lid, clamp, and heat sealer.

The purge bag may further include a second port configured to be opened and closed to let air pass through the second port. The second port may include a closing means to prevent fluid flow through the second port. The closing means may include one or more of a valve, needle-free valve, cap, lid, clamp, and heat sealer.

The fluid may be a contaminated or harmful fluid.

The details of various embodiments of the invention are set forth in the accompanying drawings and the description below. Other features and advantages of the invention will be apparent from the description, the drawings, and the claims.

DETAILED DESCRIPTION

Figure 1:
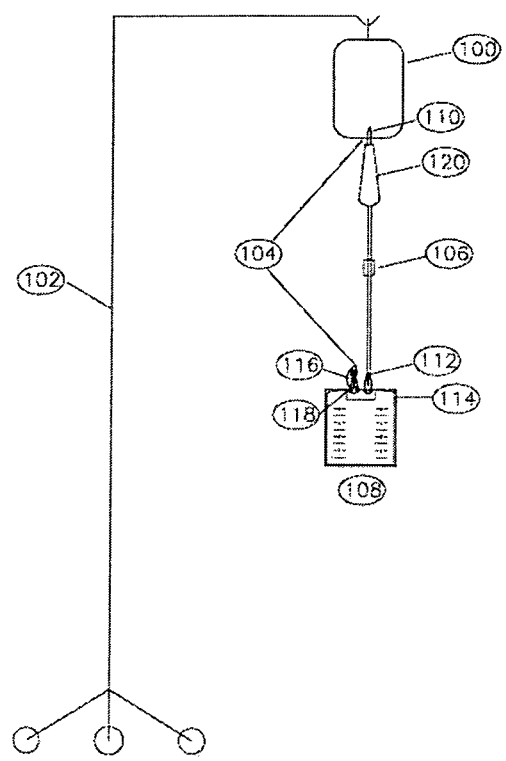
FIG. 1 is a plan view of an IV tubing system having an IV line and a fluid purge bag for purging the contents of the IV line.

The inventor has developed a system and method to address the increase in hospital-acquired infection by preventing the spillage of contaminated fluids in hospitals when intravenous (IV) lines are set up, used, and discarded. By capturing the fluids that would otherwise be spilt on the hospital floor, bed, trash can, etc., the inventor's system and method is designed to address the problems that occur when blood and blood products are spilt in the hospital, when antibiotics are spilt in the hospital, and the like. Instead of spilling contaminated fluids, the contaminated fluids are captured, handled and treated in an appropriate manner. It should be understood that contaminated fluids, as used herein, include (a) fluids that are intentionally mixed with a product, e.g., an IV bag of saline to which an antibiotic or highly potent drug substance, such as a chemotherapeutic agent, is added, (b) fluids that are useful for their intended purposes but are not considered desirable if spilt, e.g., blood or blood products, chemotherapeutic agents, antibiotics, and (c) fluids become incidentally contaminated in use, e.g., a saline flush that becomes contaminated with blood because of backflow into the IV lines. Other fluids used in hospitals or medical environments and that are not recommended for contact with humans also falls within the category of contaminated fluids.

Intravenous therapy, or IV therapy, is the administration of liquid substances directly into a vein. One well-known example of IV therapy is a peripheral IV line that consists of a short catheter (a few centimeters long) and is inserted through the skin into a peripheral vein, such as a vein located in the arm or hands. The intravenous route is the fastest way to deliver fluids and medications throughout the body, and this procedure is used numerous times daily in U.S. hospitals.

In the current hospital environment, hospital personnel setting up IV's may add a medication to an IV bag and then prior to administering the IV to a patient, purge air from the bag to removing all air from the tubing so as not to introduce air in the vasculature. In the purging step, the hospital personnel let the harmful fluids spill on the floor, bed, in the trash can, etc. This spillage of blood products, chemotherapy, and antibiotics leads to growth of bacteria and an increase in antibiotic-resistant bacteria. One of the foremost concerns in modern medicine is antibiotic resistance. Simply put, if an antibiotic is used too long or spilled over bacteria, a germ mutation can occur that results in a "super bug" which cannot be killed by that antibiotic. This is known as antibiotic resistance bacteria. In fact, some infections exist today that are caused by various bacteria resistant to some approved antibiotics. An example of such a super bug is methicillin-resistant *staphylococcus aureus* (MERSA). Another relevant term of importance in this field is nosocomial infections, which are those infection that result from treatment in a hospital or a healthcare service unit.

The existence of antibiotic-resistant bacteria creates the danger of life-threatening infections that do not respond to antibiotics. There are several reasons for the development of antibiotic-resistant bacteria. One of the most important is antibiotic overuse and misuse. Hospital personnel can help reduce the development of resistant bacteria by using a contained device such as the Intravenous Purge bag. The intravenous purge bag is attached to the intravenous tubing to receive and contain the harmful fluids rather than letting the harmful fluids be spilt.

Examples of harmful fluids include antibiotics (including anti-bacterials, anti-virals, and anti-fungals), blood products, chemo therapy agents, and total parenteral nutrition (TPN). In general, a harmful fluid is one that is either harmful in itself when not used for its intended purpose or that has the ability to result in strains of bacteria and the like that are resistant to the fluid.

In one embodiment, the intravenous purge bag is a small volume bag, e.g., 50-100 cc, more particularly 100 cc, with two ports: an air port and a connector port having a connector, such as a SmartSite needle-free valve, which is designed to fit at the end of intravenous tubing to provide a contained unit with no spillage of contaminated or harmful fluids during purging. The connector port having the connector, such as the Smartsite needle-free valve, is connected to the end of the intravenous tubing and the air port is open, opened or openable to allow air into or out of the bag to permit a good flow of fluid into the purge back from the IV tubing. Each port may have a cap, lid, or other closing means attached to the port. Once the intravenous tubing is purged of air, the caps or lids are closed and secured. The intravenous purge bag thereby contains the harmful fluids. This allows the health care professional to discard the intravenous purge bag with out spillage.

Figure 2:
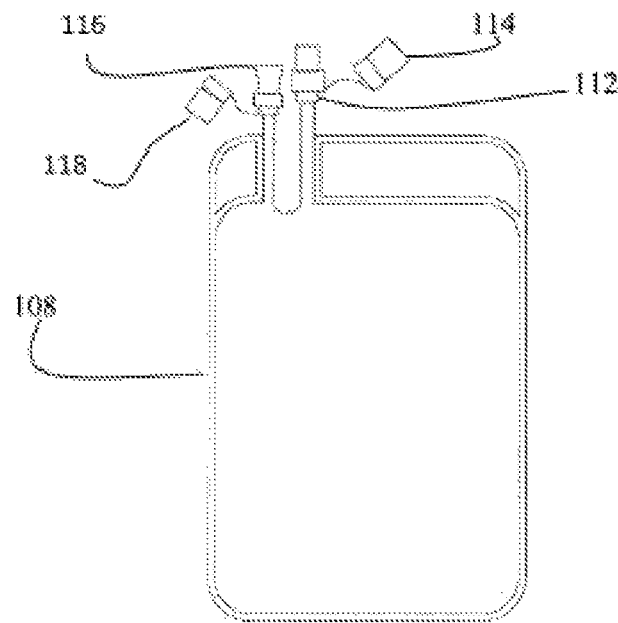
FIG. 2 is a front view of a fluid purge bag for use with the IV tubing system illustrated in FIG. 1.
Figure 3:
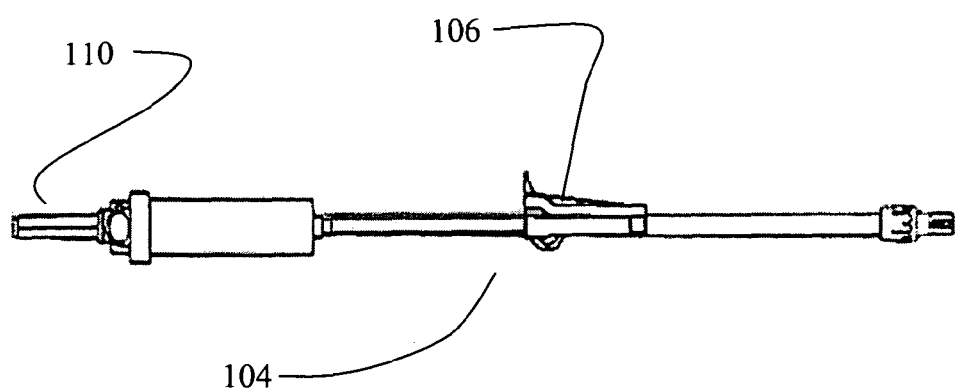
FIG. 3 is a front view of an IV line for use with the IV tubing system illustrated in FIG. 1.

Referring to FIGS. 1-3, the IV purge bag is used, for example, to administer an antibiotic, blood product, chemotherapeutic agent, or high potency compound through an IV line. In so doing, the health care professional first collects the materials needed to administer, e.g., the antibiotic: the antibiotic 100 in the form of a 50 cc to 500 cc IV bag of the antibiotic medication in a fluid such as saline, an IV pole 102, an intravenous tubing set 104, and the intravenous purge bag 108. The intravenous tubing set includes a drip chamber 120, a stop cock 106 and a spike 110 at the top of the tubing. The intravenous purge bag 108 includes a colored, e.g., blue, connector port 112 with a lid or cap 114, and a colored, e.g., white, air port 116 with a lid or cap 118. The blue, connector port 112 permits entry of fluids into the bag and the white, air port 116 allows air to escape the bag during filling of the bag when such need exists.

The IV line may be set up to deliver the antibiotic in the form of an IV drip. An intravenous drip is the continuous infusion of fluids, with or without medications, through an IV access device. This may be to correct dehydration or an electrolyte imbalance, to deliver medications, or for blood transfusion. The IV drip may be given using an IV infusion set, which generally is made up of a pre-filled, sterile container (e.g., glass bottle, plastic bottle or plastic bag) of fluids with an attached drip chamber which allows the fluid to flow one drop at a time, making it easy to see the flow rate (and also reducing air bubbles); a long sterile tube with a clamp to regulate or stop the flow; and a connector to attach to the access device.

In the procedure, the health care professional first performs hand washing, which is accepted as a must at the start of any medical procedure to maintain hygiene and prevent the spread of contaminants. The health care professional then explains the procedure to the patient and assesses the intravenous access in the patient's arm to make sure the patient receives the medication without any leakage at the site. The health care provider next opens the package that contains the intravenous tubing 104, removes the tubing from the packaging, ensures that the stop cock 106 on the intravenous tubing is closed, and then attaches the intravenous purge bag 108 at the connector port 112 (marked with a blue color code) and verifies that it is securely attached to the end of the intravenous tubing 104.

The air port 116 (marked with a white color code) on the intravenous purge bag 108 then is opened, the antibiotic medication bag 100 is spiked with the spike 110 at the top end of the intravenous tubing 104 and the bag 100 is hung on the intravenous pole 102. Once the IV medication bag 100 is accessed the drip chamber 120 is squeezed to fill half way so the health care provider can monitor the fluid dripping from the intravenous bag 100 into the drip chamber 120. The stop cock 106 is opened on the intravenous tubing 104. The antibiotic fluid flows from the bag 100 hanging on the IV pole 102 with the antibiotic in it through the intravenous tubing 104 into the intravenous purge bag 108 positioned in that order while the health care provider is holding the stop cock 106 in the one hand and the intravenous purge bag 108 in the other hand. Once the intravenous tubing 104 is free of air the health care provider closes the stop cock 106 on the intravenous tubing 104 and then disconnects the intravenous purge bag 108 from the tubing at the connector port 112. The air port lid or cap 118 is placed over the opened air end of the purge bag. With the port closed and caps or lids secure, the intravenous purge bag 108 then is discarded as a contaminated medical object and treated accordingly. The intravenous tubing 104 then is attached to the line already in the patient to receive the antibiotic medication.

The system above may have numerous modifications. For example, the size of the purge bag can be varied depending upon the application in which it is used. Purge bags can have volumes in the range of milliliters to sizes much larger. Similarly, the ports on the purge bag can be varied. For example, the air port can be valved so that squeezing the air port opens the valve and lets air out but releasing the air port permits the valve to close, which thereby retains air, as well as fluids, within the purge bag. The connector port also can be valved in a manner that opens the valve to permit connecting to the IV lines but closes when the IV line is disconnected. This configuration is designed to reduce the chance that a filled purge bag will spill its contents when the IV line is removed and/or otherwise closed.

The caps or lids to close the purge bag also can be varied. For example, the caps or lids can be replaced with a clamp-like device to close off the port. As another alternative, the purge bag can be used with a thermal sealing device that clamps and seals the ports.

Figure 4:
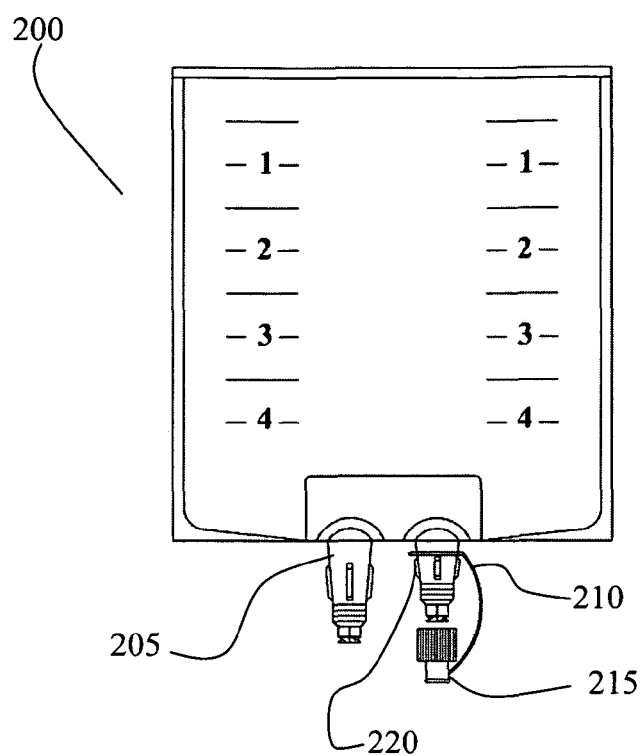
FIG. 4 is a front view of a fluid purge bag having two ports.
Figure 5:
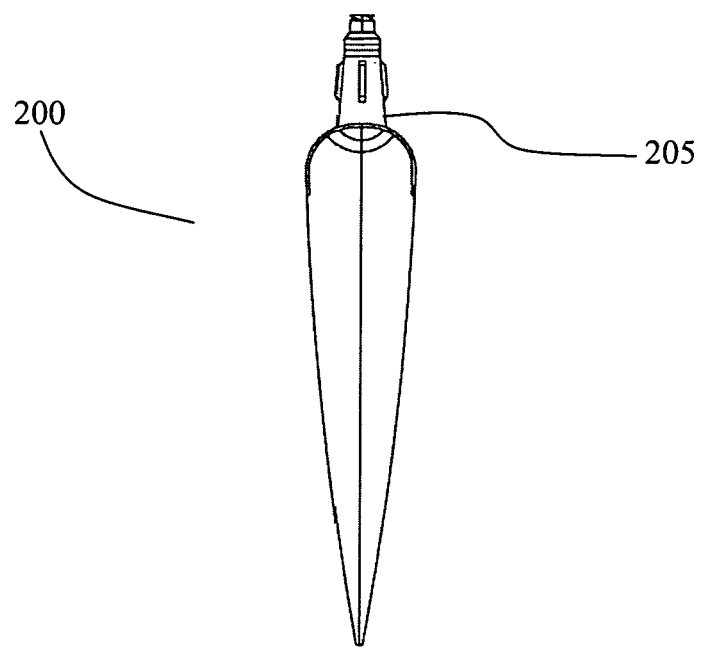
FIG. 5 is a side view of the fluid purge bag of FIG. 4.

Referring to FIGS. 4 and 5, a purge bag 200 includes a valved port 205 and a valved port 210. The valved port 205 can be, for example, a needleless valved port to which an IV fluid line from a bag containing an antibiotic is attached. Connecting the IV fluid line to the valved port opens the valve and permits the flow of fluid into the purge bag 200 but will not allow fluid flow out of the purge bad. One example of a needless valved port is a Smartsite® needle-free valve available from B. Braun Medical. The valve can be part of the port or be the port into the bag. The valved port 210 can include a cap 215 and a stem 220 that opens into the bag. The port 210 is used to let air out of the bag 200 when it is being filled.

Figure 6:
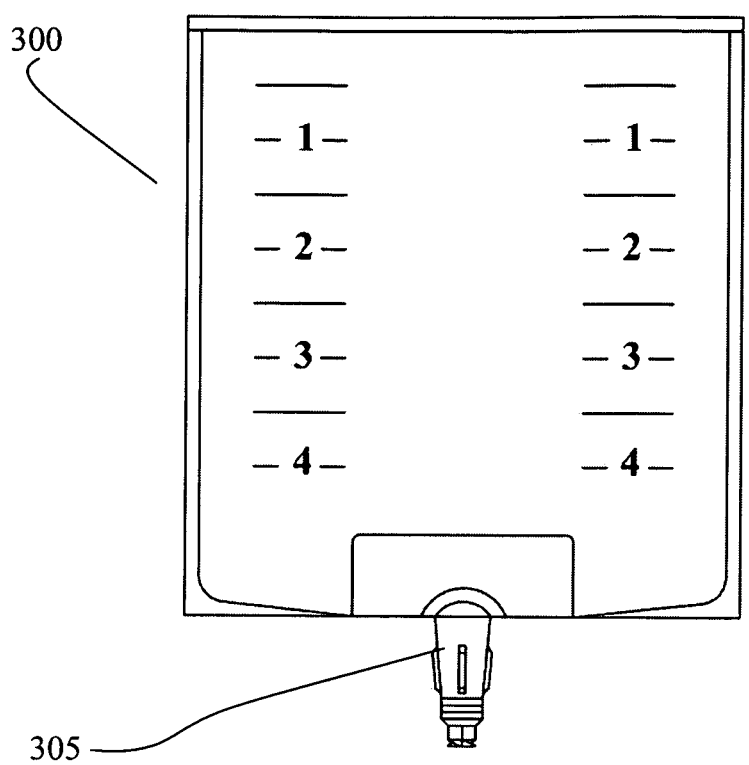
FIG. 6 is a front view of a fluid purge bag having one port.

Referring to FIG. 6, a purge bag 300 includes a valved port 305 for connecting to an IV fluid line. The valved port 305 may be a needleless port such as the Smartsite® described above. The purge bag 300 differs from the purge bag 200 as it does not have a second port, such as a valved or needleless port. In the embodiment of FIG. 6, the lack of a second port for letting out air is acceptable when the amount of air in the bag is sufficiently small such that filling purge fluid into the bag does not result in a pressure level in the bag that prevents fluid filling into the bag. One advantage of the purge bags 200 and 300 are their valved ports which allow the ports to be closed automatically as a failsafe against the medical professional failing to close a port and thereby allowing fluid to spill from the bag.

In conclusion the intravenous purge bag is a valuable tool against the increasing rate of hospital acquired infections and pharmaceutical resistant medical conditions. If this product is used worldwide it can provide the same advantages on a global scale. This product is an effective cost and a life saving method. The cost the hospitals constantly face and the lives lost due to the high rate of nosocomial infections are both problems that the inventor believes can be addressed by using this device. Further, the inventor believes that introducing the intravenous purge bag to the health care population will decrease infection rates dramatically. In one embodiment, the purge bag is part of a kit that includes the IV tubing and may be provided already attached to the IV tubing. In this manner, the health care provider by default will have the purge bag set up to receive the fluids and must actively modify the IV tubing set to use it without the purge bag or the purging step. In another embodiment, the purge bag is packaged separately from the IV tubing set and both packages opened at the time of use. The purge bag may be supplied with the drug by the drug manufacturer, which may wish to ensure that the drug is not spilt or discarded on the floor in use at a hospital. For example, the drug may be supplied as a powder or solution along with the purge bag and complete IV set.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

What is claimed is:

1. A method of purging an IV tubing system, the method consisting of providing an intravenous tubing system and a purge bag to prevent spillage of fluids comprising:
    an intravenous tubing comprising a first end configured to attach to a fluid container and a second end having a connector; and
    providing in an unconnected state a purge bag, the purge bag having at least one port configured to attach to the connector and the port including a closing means to close the port to prevent fluid flow through the port out of the purge bag, the port being openable to receive fluids from the intravenous tubing into the purge bag and closable by use of the closing means to prevent flow of fluids out of the purge bag through the port;

attaching the purge bag to the IV tubing;

attaching the intravenous tubing to a fluid container containing a fluid to be administered to a patient;

purging a portion of the contents of the fluid and air in the intravenous tubing through the port into the purge bag until the intravenous tubing system is free of air in the line passing between the fluid container containing the fluid and the second end of the intravenous tubing;

disconnecting the intravenous purge bag from the tubing at the connector port, closing the port with the closing means and discarding the purge bag without fluid escaping from the purge bag through the port; and attaching the intravenous tubing to a line for connecting to a patient to receive the fluid from the fluid container.

2. The method of claim 1, wherein the IV tubing set and the purge bag are provided with the connector of the IV tubing set connected to the at least one port of the purge bag.

3. The method of claim 1, wherein the IV tubing set and the purge bag are provided unconnected and the connector of the IV tubing set is connected to the at least one port of the purge bag.

4. The method of claim 1, wherein the closing means comprises one or more of a valve, needle-free valve, cap, lid, clamp, and heat sealer.

5. The method of claim 1, wherein the purge bag further comprises a second port configured to be opened and closed to let air pass through the second port.

6. The method of claim 5, wherein the second port includes a second closing means to prevent fluid flow through the second port.

7. The method of claim 6, wherein the second closing means comprises one or more of a valve, needle-free valve, cap, lid, clamp, and heat sealer.

8. The method of claim 1, wherein the fluid comprises a contaminated or harmful fluid.

9. The method of claim 1, wherein the method comprises of providing an intravenous tubing system and a purge bag to prevent spillage of fluids consisting essentially of:

an intravenous tubing comprising a first end configured to attach to a fluid container and a second end having a connector; and a purge bag, the purge bag having at least one port configured to attach to the connector and the port including a closing means to close the port to prevent fluid flow through the port out of the purge bag, the port being openable to receive fluids from the intravenous tubing into the purge bag and closable by use of the closing means to prevent flow of fluids out of the purge bag through the port;

attaching the intravenous tubing to a fluid container containing a fluid to be administered to a patient; and purging a portion of the contents of the fluid and air in the intravenous tubing through the port into the purge bag until the intravenous tubing system is free of air in the line passing between the fluid container containing the fluid and the second end of the intravenous tubing;

disconnecting the intravenous purge bag from the tubing at the connector port, closing the port with the closing means and discarding the purge bag without fluid escaping from the purge bag through the port; and attaching the intravenous tubing to a line for connecting to a patient to receive the fluid from the fluid container.

* * * * *